(12) United States Patent
Metelski

(10) Patent No.: US 6,691,960 B2
(45) Date of Patent: Feb. 17, 2004

(54) STAND

(75) Inventor: Andrzej Metelski, Romanshorn (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 10/007,168

(22) Filed: Nov. 8, 2001

(65) Prior Publication Data

US 2002/0121578 A1 Sep. 5, 2002

(30) Foreign Application Priority Data

Nov. 12, 2000 (DE) ..................... 200 19 107 U

(51) Int. Cl.⁷ ................................. A47F 5/00
(52) U.S. Cl. ..................... 248/123.2; 254/374
(58) Field of Search ............. 248/125.2, 123.11, 248/123.2, 648, 550; 254/278, 374, 391; 242/388.9, 390.4

(56) References Cited

U.S. PATENT DOCUMENTS

| | | | | |
|---|---|---|---|---|
| 4,344,595 A | * | 8/1982 | Heller et al. | 248/542 |
| 4,512,106 A | * | 4/1985 | Roche | 49/445 |
| 4,605,189 A | * | 8/1986 | Bruneau | 248/162.1 |
| 5,173,802 A | * | 12/1992 | Heller | 359/384 |
| 5,205,522 A | * | 4/1993 | Nakamura | 248/123.11 |
| 5,253,832 A | | 10/1993 | Bolas et al. | |
| 5,397,323 A | | 3/1995 | Taylor et al. | |
| 5,538,209 A | * | 7/1996 | Bowden et al. | 244/221 |
| 5,551,652 A | * | 9/1996 | Verhoeven | 244/220 |
| 6,070,839 A | | 6/2000 | Brenner et al. | |
| 6,129,319 A | * | 10/2000 | Metelski | 248/123.2 |

FOREIGN PATENT DOCUMENTS

| | | |
|---|---|---|
| DE | 3444313 | 8/1985 |
| DE | 3739080 | 5/1989 |
| DE | 19742050 | 3/1999 |
| EP | 0866269 | 10/1999 |
| WO | WO97/13997 | 4/1997 |

* cited by examiner

Primary Examiner—Korie Chan
(74) Attorney, Agent, or Firm—Hodgson Russ LLP

(57) ABSTRACT

The invention relates to a stand having a support arm (2) and a balance weight (AG), which, via at least one cable pull (24d,f), ensures the weight compensation of the load (G), at least a second cable pull (24f) and/or at least a safety cable (324) and possibly at least one braking device (39; 42; 45; 57) being provided as a safety measure against breakage of the working cable (24d).

22 Claims, 8 Drawing Sheets

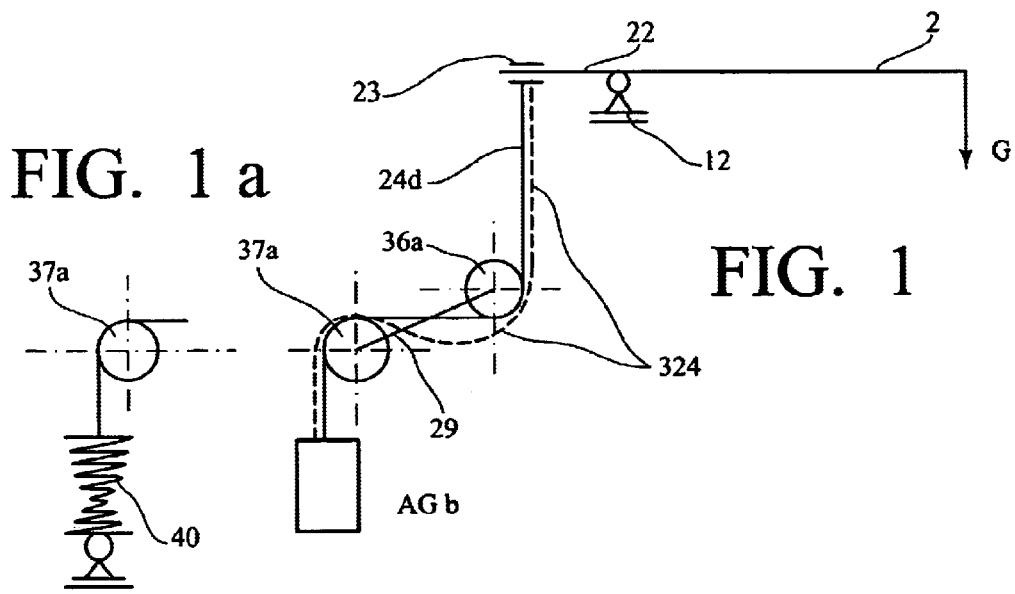
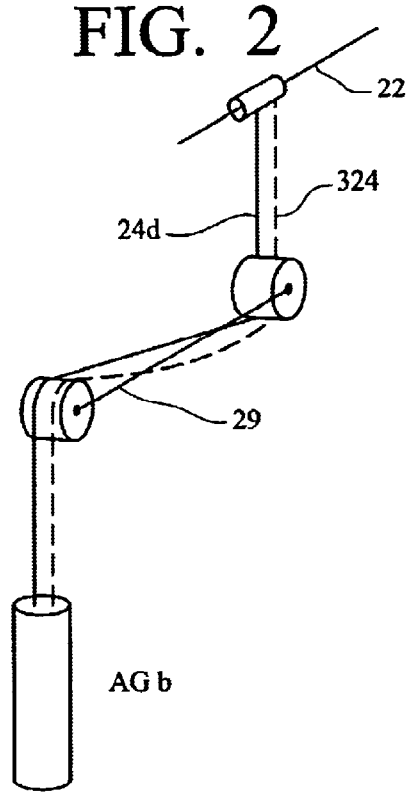
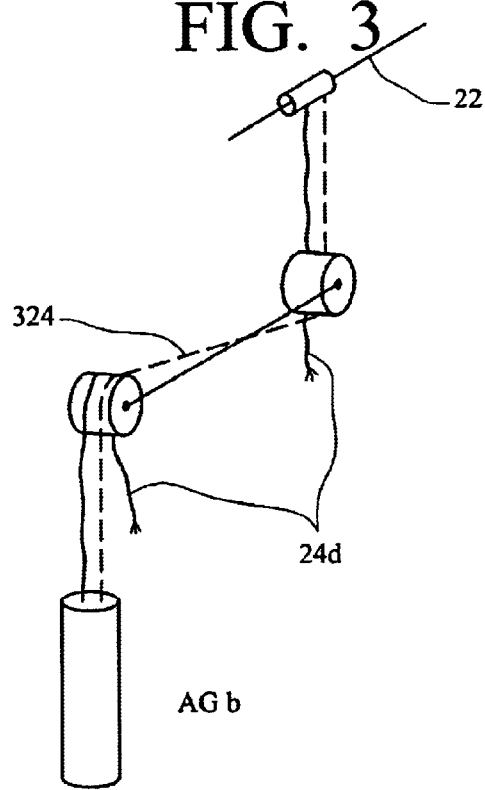
FIG. 1a
FIG. 1
FIG. 2
FIG. 3

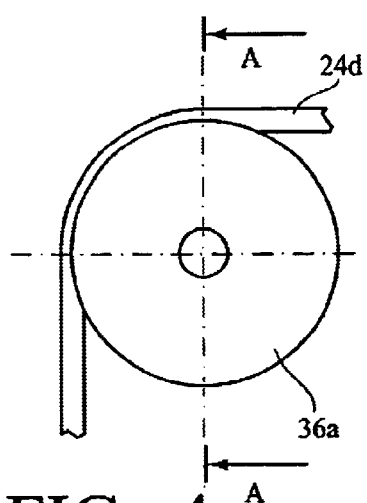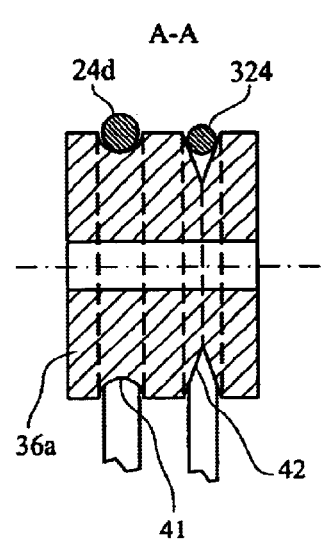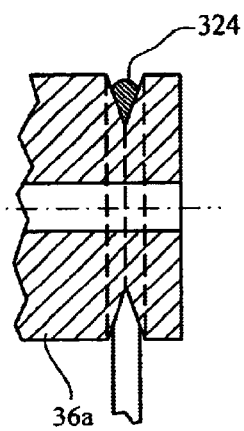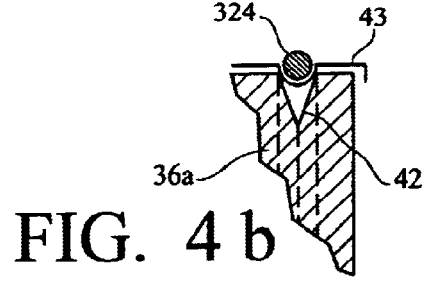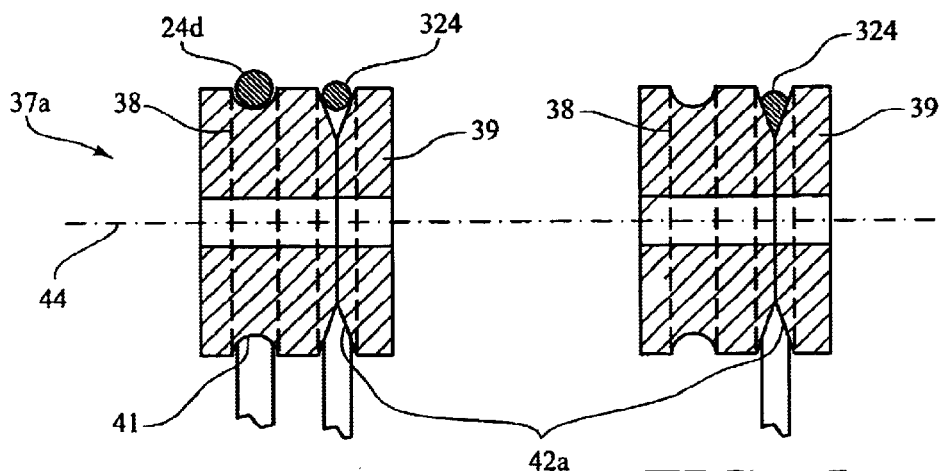

STAND

CROSS REFERENCE TO RELATED APPLICATIONS

This invention claims priority of the German application 200 19 107.1 filed Nov. 12, 2000 which is incorporated by reference herein.

FIELD OF THE INVENTION

The invention relates to a stand, in particular for surgical microscopes, of the type having a pivotable support arm (2) to accommodate a load (G) and having a balancing force (FA) which acts on the support arm (2) via a working cable pull (24).

BACKGROUND OF THE INVENTION

Surgical microscopes must be capable of being pivoted easily over a predefined range and should maintain a set position. For this reason, in the case of known stands, balance weights or compensation springs are provided, which compensate for the weight of the microscope and its additional devices. The balance weights are most frequently arranged in the manner of beam-type balances.

Particular embodiments of such beam-type balance arrangements are, for example, the "OHS(™)" design of the applicant, in which balance weights are displaced by parallelogram carriers from the top to the lower region of the stand, so that the overall centre of gravity of the stand is situated in the lower third of the stand structure. The basic construction of the OHS(™) is illustrated symbolically in the international patent application WO 97/13997 of the applicant. In the case of this construction, rods form the connection between the support arm and balance weight.

The invention is concerned in particular with the question of increased operational safety in stands. The following statements from the prior art show that, hitherto there are still no optimum safety precautions in the event of material fractures for cable-assisted but also for other microscope stands.

In DE 197 42 050 A1, reference is made to an article "Gewichtsausgleich an feinmechanischen Geräten [Weight compensation in precision mechanical devices]" by H. Hilpert in Volume 2/1965 of the publication Feingerätetechnik [Precision Engineering], Volume 14.

In this article from the year 1965, various weight-compensating measures in precision engineering are discussed, being achieved primarily not by means of a counterweight but by means of spring-compensating measures (such as, by way of comparison, also in the scissors-arm construction of the MS 1 design from the applicant). In this case, safety aspects do not play any part.

DD 221571 A1 (1985) shows a stand design having a lever arm, at whose distal end there is a surgical microscope. The weight of the microscope is compensated for by a spring, which is connected to the lever arm via a cable pull. The basic adjustment of this surgical microscope is carried out by means of a threaded spindle, with which the end of the spring on the housing side is pulled further away from the lever arm or led closer to it. Changes in weight at the microscope are compensated for by the fact that the pivoting point of the cable pull is likewise adjusted relative to the lever arm via a spindle.

In order to achieve a uniform countermoment in all possible angular positions, it is necessary for the abovementioned point of action of the cable pull to be located on a connecting line between the axis of rotation of the lever arm and the mass centre of gravity of the microscope. This is achieved by operating an adjusting device in the form of a worm, which rotates a disc connected to the lever arm about the axis of rotation of the lever arm.

DE 3739080 A1 (1989) likewise specifies a spring device for balancing the weight for stands, in which cable pulls combined with springs are intended to lead to balancing. However, this concerns using force to support an adjusting movement which is exerted by an operator on a handle and not holding a load in a "floating state", as is desired in surgical microscopes. In the case of breakage of the spring or of the cable, the weight compensation disappears, and the load can fall suddenly.

By contrast, U.S. Pat. No. 5,397,323 (1992) presents a surgical robot with parallelogram carriers, in which, inter alia, the weight of the instrument is held in a weight-compensated fashion via a cable pull with the aid of a counterweight. The cable pull is of closed design in this case, that is to say one cable in each case is guided from the instrument up to the counterweight over an upper and lower deflecting roller (FIG. 3 of U.S. Pat. No. 5,397,323).

DE 19742050 A1 (1999) discloses a stand design having a pivotable parallelogram carrier which is weight-compensated via a cable pull and a balancing spring such that the balance weights which are additionally present and which act in accordance with the abovementioned principle of the balance can be designed to be particularly small. In this design, the cable pull is guided in a special way in order to minimize the balancing error, caused by the finite deflecting radius, in a wide pivoting range of the pivoting arm. The balancing error is, however, not eliminated by this measure, and so in specific pivoting positions it remains necessary to adjust the balance weights.

U.S. Pat. No. 6,070,839 (2000) discloses a further design having a pivoting arm and a cable pull-spring construction which permits pure balancing. In the case of changes in the weight, the pivoting point of the cable pull is displaced, in a fashion comparable to the design in the abovementioned DD 221571, over a spindle. A material fracture which may occur is not treated in this document.

U.S. Pat. No. 5,253,832 (1999) describes a stand having a cable pull and a centrally arranged tension spring for the balancing. This design offers no simple adjustability for changed loads. The cable accepts all of the load of the carrying arm and of the microscope.

In a design according to EP-A-866269, in order to transmit balancing weights, use is made of a toothed belt which can be kept braked by means of a brake. If a breakage occurs in the toothed belt, this can lead to the microscope falling onto the patient lying underneath it on the operating table.

All of the stand designs known hitherto and specified above, having cable pulls or toothed belts, have the same problems: in the event of breakage of the cable or of a tension spring, there is considerable disruption to the functioning of the instrument, which as a rule can lead to the sudden lowering of the load, and in the case of a surgical microscope to rapid, impermissible lowering of the microscope.

In particular during an operation, such a breakage could have catastrophic consequences for the patient. The obvious solution would be to dimension the cable used to be correspondingly thick, so that a breakage is virtually impossible. However, as the material thickness increases, the cable pulls become less mobile.

In questioning the dimensioning, it is also necessary to take account of the fact that, in extreme situations, the load or the weight on the load action point can rise in an extremely high manner. This is the case, for example, when a surgeon—for example perhaps because of nausea—supports himself briefly on the microscope.

SUMMARY OF THE INVENTION

The invention is, then, based on the object of finding a safety mechanism which, in the event of a cable breakage, does not lead to the load being lowered. The invention is in this case not to be restricted merely to the use in a stand for surgical microscopes, but instead to any desired forms of stand in which force and/or balance compensation is performed by means of cable pulls.

This object is achieved by the provision of at least a second cable, the second cable being designed to be equivalent to the first cable and, in parallel, exerting the same functions as long as the first cable is intact. In the safety case (that is to say breakage of one of the two cables), it performs the working cable function on its own.

Alternatively, at least a second cable is placed to the side of the at least one working cable as a safety cable, being untensioned in the operating state and performing the functions of the working cable only in the safety state. According to the invention, this leads to the working resistance being substantially no higher than in the case of designs with only one cable, in spite of the use of two cable pulls, since the safety cable runs along virtually without friction and therefore without resistance.

In the sense of the invention, the term "cable" comprises all those design elements which are of cable-like, belt-like or chain-like design and serve to transmit load.

In the event of breakage of the working cable there is therefore only a minimum movement of the load (until the safety cable is tensioned), which therefore as a rule does not constitute any hazard. In the case of equivalent working cables without an actual safety cable, adaptation in the safety case is, if appropriate, likewise carried out via a rocker-like component—preferably with limitation of the travel in order to limit the rocker movement.

According to a special refinement of the invention, a further safety mechanism is provided which is intended to prevent the stand continuing to be used over an unrestricted time period, although a working cable has been broken. Without this further safety mechanism, the operator would notice virtually no difference between working with the working cable and working with the safety cable. In the case of the broken working cable, according to the fundamental design of the invention, the device runs unchanged as before with the intact working cable, but with a loose safety cable. The further safety device provides that, as soon as the safety cable is active, a brake automatically comes into function which considerably increases the working resistance at the instrument, that is to say the resistance detected by the user when pivoting the load.

This high working resistance is intended to indicate to the user that the instrument must be subjected urgently to a service. In the course of the service, the broken working cable can then be replaced and the original state reproduced. However, the working resistance is not so high that an operation has to be interrupted or aborted because of the non-operability of the stand.

In a special refinement of the invention, the second safety mechanism is activated automatically, by the safety cable, which is originally not loaded, being loaded in tension. As soon as it is loaded in tension, the safety cable is forced into a wedge-like groove in a deflecting roller, in which it is subjected to a high frictional resistance. This is as distinct from a conventional throat-like running groove for the working cable, which opposes as little frictional resistance as possible to the cable run. The wedge-like groove can be protected, by means of a protective film made of plastic, metal or the like, against the cable inadvertently biting into the wedge groove, the said protective film only breaking and opening the path to eat into the wedge groove when a tensile force of a specific magnitude is exerted on the safety cable.

An alternative variant to the aforementioned design with an additional safeguard is a clamping element, which is arranged in a relative position in relation to the safety cable such that, in the unloaded state, the said safety cable passes loosely through the clamping element while, in the loaded state (in the tensioned state), it penetrates into the clamping element and is subjected there to increased friction.

The safety cable therefore interacts with a braking element which—when the safety cable has taken over the pulling function in the event of breakage of the working cable—brakes the safety cable or a component connected to it, so that only emergency operation of the stand is still possible. The braking element can be a dedicated cable pinch brake (such as, for example, in the case of a sailing ship) but can also be a ratchet brake (as in an automatic safety belt) or a running roller with a particularly deep V groove or the like.

This design can be improved still further by a development by the safety cable being kept pressed in the loose direction by a tensioner, the tensioner being spring-loaded with a relatively low spring force which, in the event of cable breakage of the working cable, can easily be overcome by the tension in the safety cable.

The present invention will preferably be used in the case of a stand design according to the commonly owned patent applications DE 200 19 109, DE 200 19 105 and DE 200 19 106 (respectively corresponding to U.S. patent applications Ser. Nos. 10/010,103, 10/010,101, and 10/008,285) filed on the same date. However, it is not restricted to such designs. For the purpose of the possible later combination of at least two of the three patent applications, the disclosures in the above-listed applications are incorporated by reference into the disclosure of the present patent application.

Supports in the sense of the patent claims are to be understood both as individual support arms and also parallelogram carriers or similar constructions.

BRIEF DESCRIPTION OF THE DRAWINGS

In the following text, the invention is explained in more detail by way of example using drawings, in which:

FIG. 1 shows the principle of the design of a stand with support arm, sliding pad, cable pull and parallel-guided safety cable pull;

FIG. 1a shows a variant with a spring pull;

FIG. 2 shows the normal working state of the design according to FIG. 1 in a perspective view;

FIG. 3 shows the safeguarded state of the design according to FIG. 1, with a broken working cable;

FIG. 4 shows a deflecting roller with the two cables;

FIG. 4a shows a detail from FIG. 4;

FIG. 4b shows a variant of FIG. 4a;

FIG. 4c shows a cross-sectional view of the deflecting roller taken generally along the line A—A in FIG. 4;

FIGS. 5 and 5a show a multi-part variant of a deflecting roller;

FIGS. 12 and 12a show a variant with an electrical limit switch for the emission of a signal and/or control of the brake in the safety case; and FIGS. 13 and 13a show a variant of the design according to FIG. 8, in which only two working cables 24d are provided, which are in principle always tensioned.

The figures are described in an overlapping fashion, identical reference symbols signifying identical components, reference symbols with the same numbers but different indices signifying slightly different components with identical tasks and/or similar effects.

DETAILED DESCRIPTION OF THE INVENTION

Figure 6:
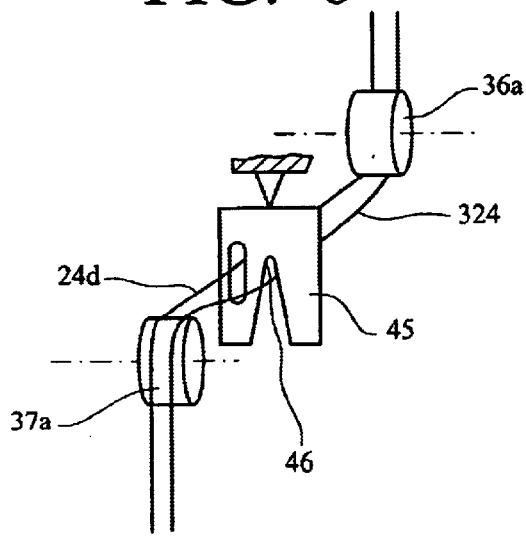
FIGS. 6 and 6a show an alternative design with a wedge brake which is not connected to the deflecting rollers.
Figure 6A:
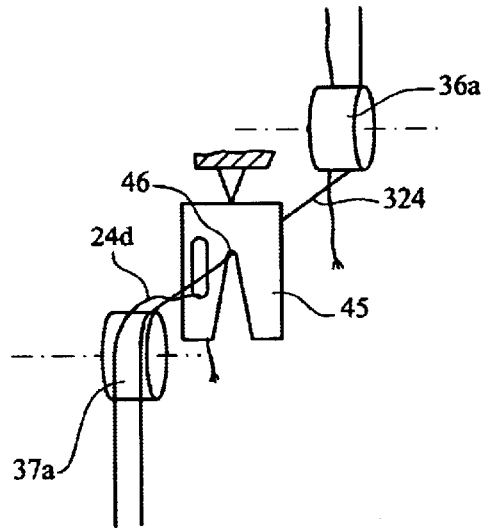

FIG. 1 shows a stand with a support arm 2, balance arm 22 and sliding pad 23 which can be displaced on the latter, which has been left out of FIGS. 2 and 3. As a rule, a design according to the invention will be constructed with a sliding pad, but variants with fixedly mounted cable pulls 24 or safety cables 324 also lie within the scope of the invention.

Alternatively, a design according to the application DE 200 19 105 is also preferred, in which the sliding pad 23 is replaced by a transmission element—in particular a roller (30)—which supports a bracket (32) to which the cables 24 and 324 are fixed. The two cables are led over deflecting rollers 36a and 37a which, as distinct from the deflecting rollers designated by 36 and 37 there according to FIG. 7 of the aforementioned patent application DE 200 19 105, are guided on a double track, so that both the working cable 24d and the safety cable 324 have a track groove available.

At the lower end of the two cable pulls 24d and 324, these are connected to a balance weight AGb, which, with a constant force F loads the balance arm 22 in the balancing direction, via the cable pull 24d, with a moment which is generated by the load G and the support arm 2.

As an alternative to the weight AGb, within the context of the invention, a tension spring 40 or the like could also be provided, as indicated symbolically in FIG. 1a. Between the two deflecting rollers 36a and 37a it is possible to see the tensioned working cable 24d and the loosely hanging safety cable 324. The safety cable 324 is shown dashed, in order to emphasize it visually from the working cable 24d.

In the design according to FIG. 4, it can be seen that the groove 41 for the working cable 24d is matched to the cross section of the working cable, while the clamping groove 42 has a wedge-like cross section and the safety cable 324—if under tension—is jammed firmly under high friction in the inner region of the clamping groove 42, as indicated, for example, in FIG. 4a.

One variant to a simple wedge groove as a clamping groove 42 is represented by the design according to FIG. 4b, in which a safety jacket 43 is placed over the clamping groove 42 and bears the safety cable 324 as long as the latter rests without force on the roller 36a. However, as soon as the safety cable 324 takes over the function of the working cable—following breakage of the working cable 24d—the slightly brittle or elastic safety jacket 43 will clear the way for the safety cable 324 to jam firmly in the clamping groove 42.

The deflecting roller 37b in the exemplary embodiment according to FIG. 5 is divided into two parts 38, 39 fixed beside one another on an axis 44. The rigid part 39 could also be mounted on the axis 44 so as to be rotatable but heavily braked. In normal operation, the roller 38 therefore rotates unimpeded and the working cable 24d transmits the tensile forces. In the safety case, that is to say when the working cable 24d breaks, the safety cable 324 jams in between the freely rotatable roller 38 and the braked or rigid roller 39. This leads, as can be seen in FIG. 5a, to the braking effect in the wedge-like gap between the rollers 38 and 39. The braking action on the brakable roller 39 can, for example, be implemented in three different ways:

a) The part 39 can be fixed to the housing.

b) The part 39 can be displaced axially with respect to the part 38 and, as a result, pressed into or against a brake. The axial displacement is typically produced by the safety cable 324 biting in the safety case, since it generates a spreading action via the wedge face. The parts 38 and 39 can be spring-loaded towards each other.

c) The part 39 is assigned a brake which acts from the outside and which brakes when required—possibly controlled by a sensor.

In any case, according to the invention, a safety jacket 43 according to FIG. 4b can also be provided in the design according to FIG. 5.

In the design according to FIG. 6, a wedge brake 45 is mounted fixed to the housing, between the two rollers, and in the safety case comes into use by the safety cable 324 being tensioned and biting into the wedge groove 46 of the brake. This wedge brake 45 may replace the above-described braking possibilities according to FIG. 5.

Figure 7:
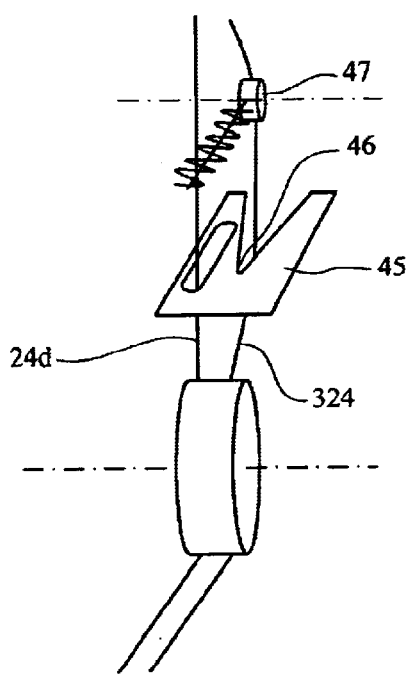
FIGS. 7 and 7a show a comparable design to FIGS. 6 and 6a with a clamping element arranged on a cable pull that runs vertically.
Figure 7A:
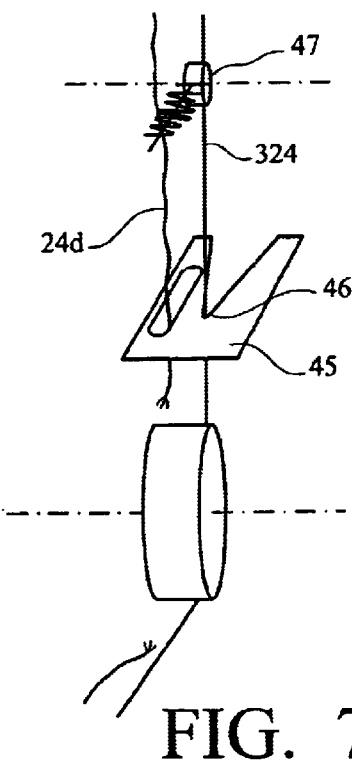

In the design according to FIG. 7, the wedge brake 45 is arranged horizontally in order to clamp the safety cable 324 running vertically there. Since, in the case of a vertically suspended safety cable 324, it is not ensured that it comes to lie on the wedge groove 46 of the wedge brake 45, in this embodiment a pressure roller 47 is preferably provided which, spring-loaded, presses the safety cable 324 into the unbraked position. The spring force applied by the pressure roller 47 is so low that it is overcome by an extremely small rise in tension on the safety cable 324, and the safety cable 324 bites into the wedge groove 46.

Figure 8:
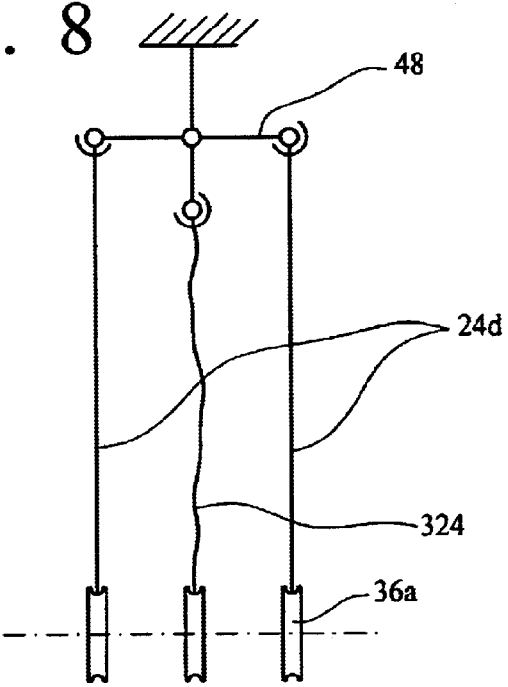
FIG. 8 shows a further variant to increase safety additionally in a design in which the balancing is performed with a plurality of cables.

In the design according to FIG. 8, two working cables 24d run in parallel and are accompanied by a central safety cable 324. A rocker 48, to which the three cables 24d and 324 are fixed, permits optimal length balancing and prevents non-uniform loading on a non-visible counterweight occurring in the event of breakage of a working cable 24d. The three deflecting rollers 36a illustrated could preferably also be formed in one piece.

In the case of only two working cables 24d without an additional safety cable 324, the rocker 48 likewise performs a balancing function in the event of breakage of one of the two working cables 24d.

Figure 9:
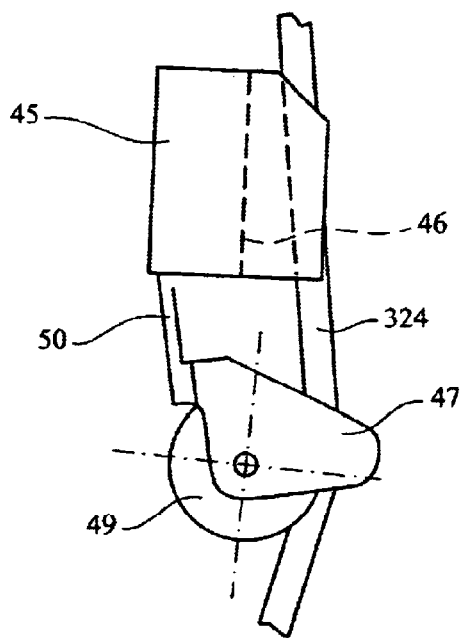
FIGS. 9 and 9a show a cable brake in the working and safe position.
Figure 9A:
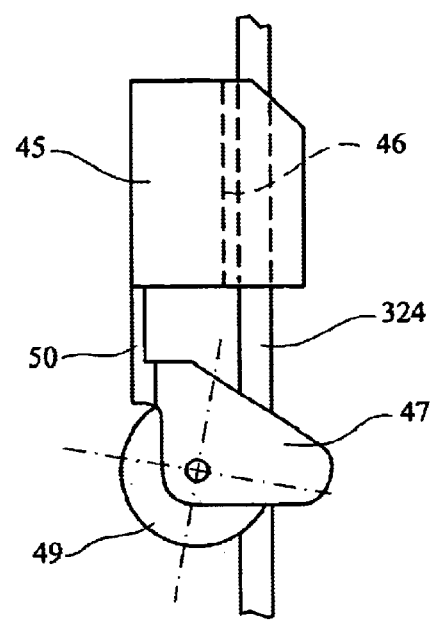
Figure 10:
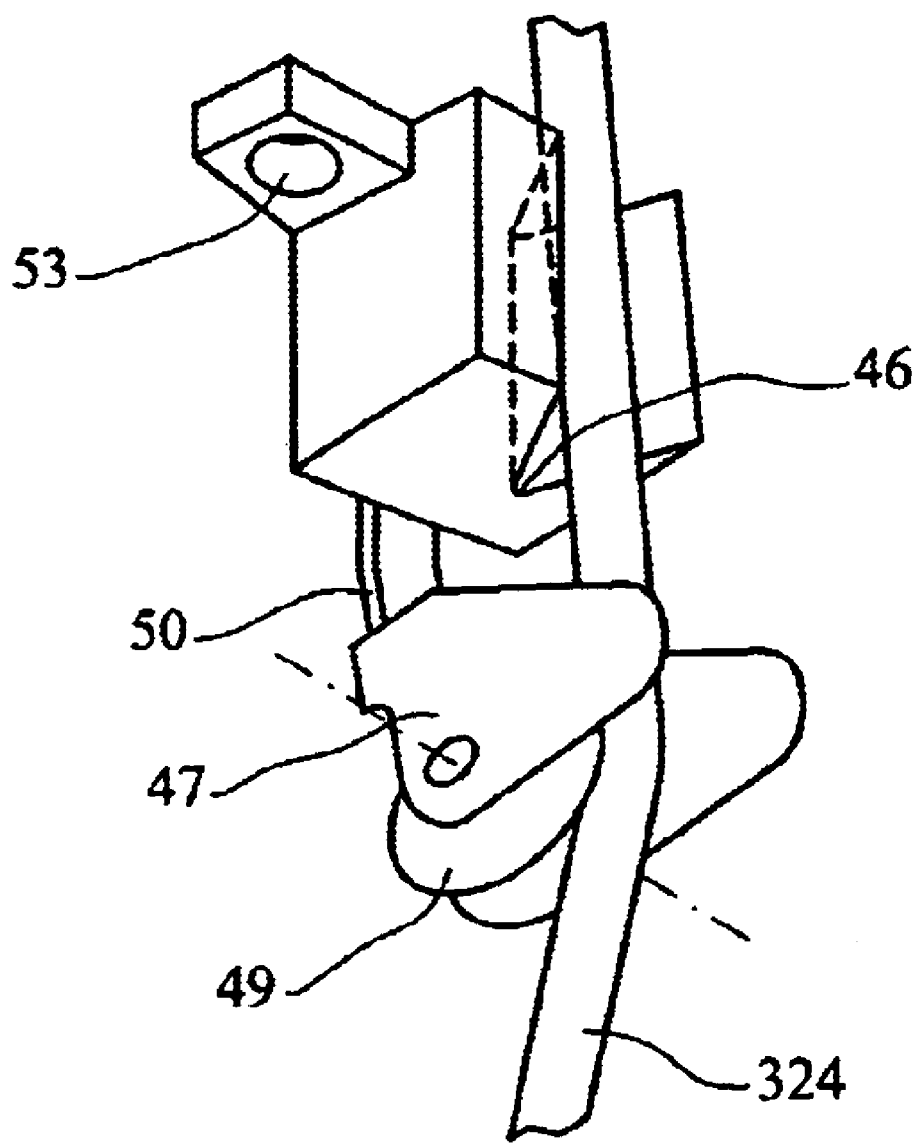
FIG. 10 shows a cable brake for the safety cable; in a perspective view.
Figure 11:
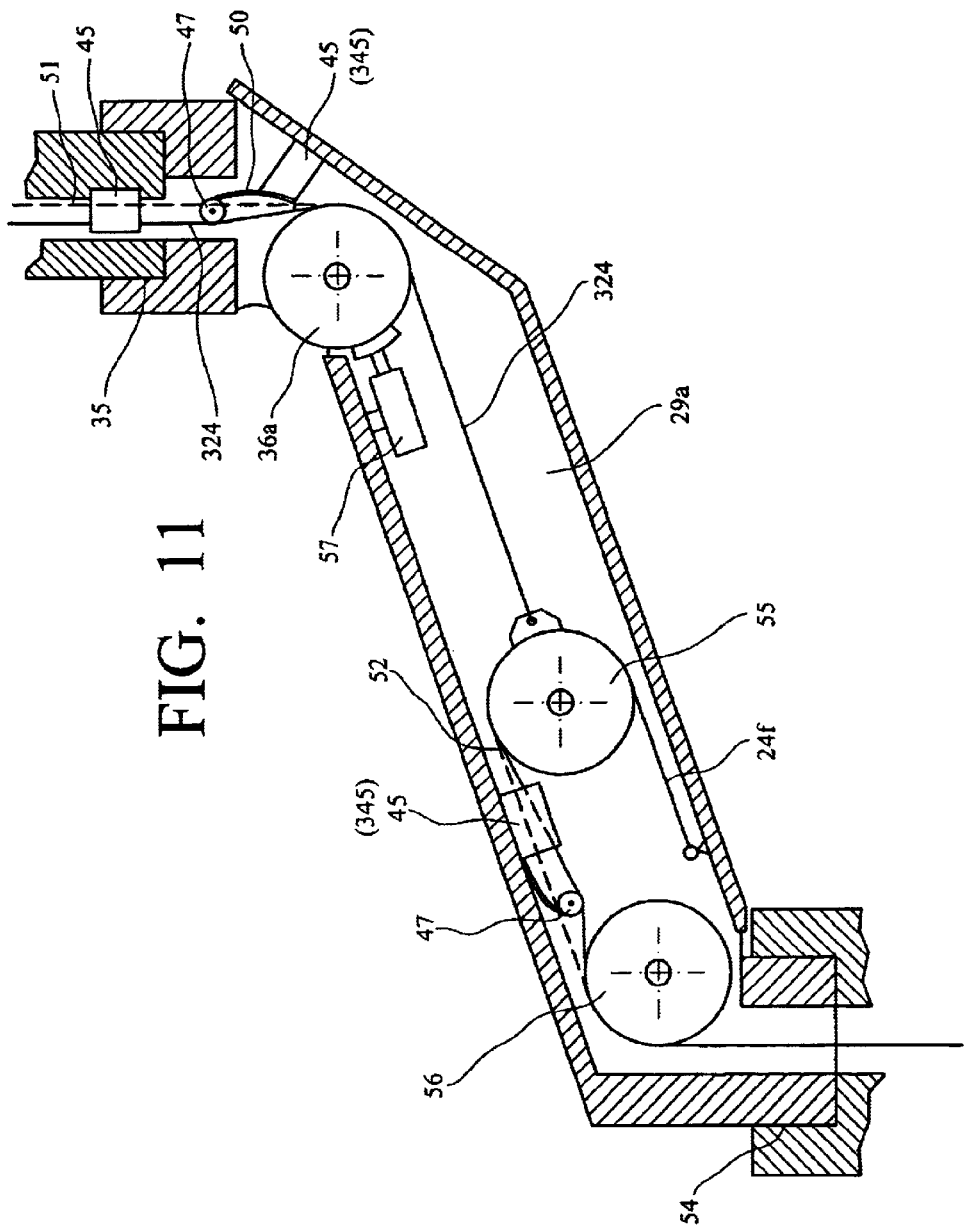
FIG. 11 shows a longitudinal section through a support arm with cable and block and tackle.
Figure 12:
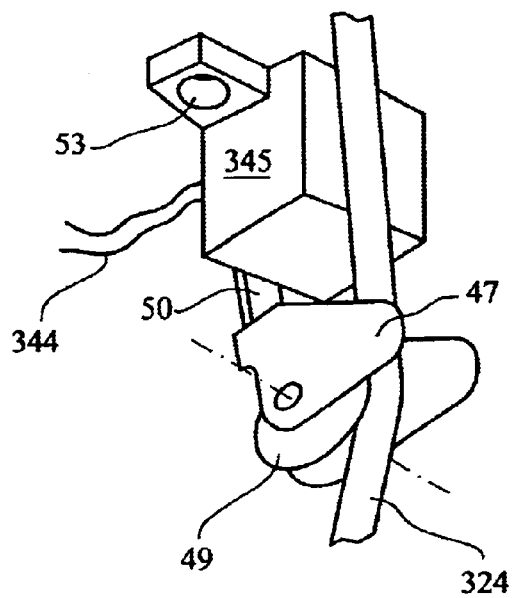
Figure 12:
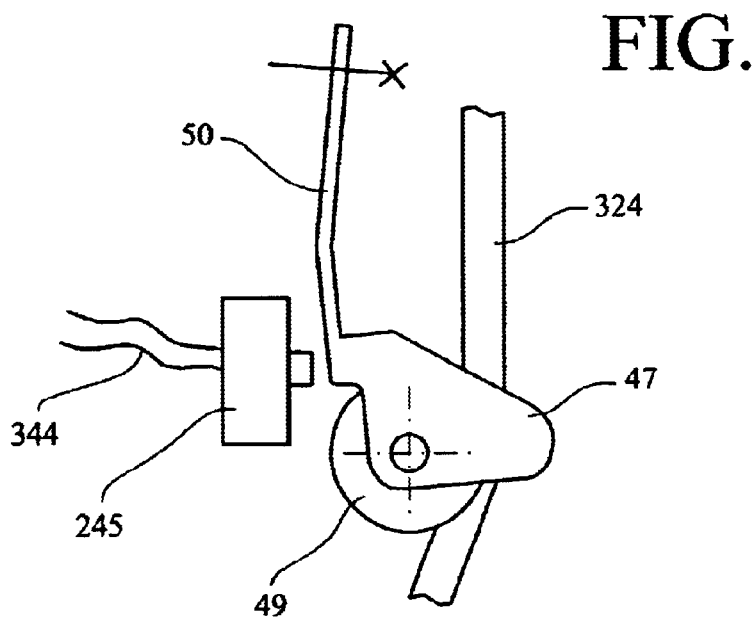

FIGS. 9 and 10 show a safety cable pull 324 which runs approximately vertically, for example as in the right-hand region in FIG. 11 or in FIG. 8. In order that this cable pull 324 does not inadvertently bite into the wedge brake 45, or into its wedge groove 46, it is kept at a distance from the wedge brake 45 by a spring-loaded roller 49. A leaf spring 50 generates the spring force.

FIG. 11 shows an extended design, such as can be connected, for example at a bearing point 54, to an upright tube of a stand. In the hollow support arm 29a there is a block and tackle 52 on which, inter alia, the safety cable 324 acts. The block and tackle 52 comprises two block and tackle rollers 55 and 56, around which the cable pulls are guided. At least one of these is a safety cable pull 24f. The latter is also assigned a wedge brake 45 with a pressure roller 47, in order to brake the safety cable pull 24f in the event of breakage of a cable pull in the block and tackle.

Pivotably mounted on a bearing 35, but not shown here, are, for example, the support arm 2 and a counterbalancing transmission. A cavity 51, which leads the cable pulls from top to bottom, runs centrally through the bearing 35. For the safety cable 324, the pressure roller 47 is provided, which keeps the untensioned safety cable 324 away from the wedge brake 45. Only in the safety case does the cable 324 press against the roller 47 or, overcoming the force of the spring 50, into the wedge groove 46 in the wedge brake 45 and therefore makes the operation of the stand more difficult.

A symbolically illustrated brake 57 permits the deflecting roller 36a to be blocked and, as a result, permits the stand to be fixed in its position. According to a development of the invention, instead of or in addition to the braking devices (for example wedge brake) illustrated, an electrical or electronic limit switch 345 or 245 can be provided which, in the safety case, responds as a result of the tension on the safety cable 324 and, via connecting cable 344, exerts a corresponding influence on a circuit connected to it. Such a circuit can, for example, activate optical or acoustic signals and/or brakes or the like. For example, provision could be made that, if electromagnetic brakes are used, these cannot be released or are moved into the braked position.

Figure 13:
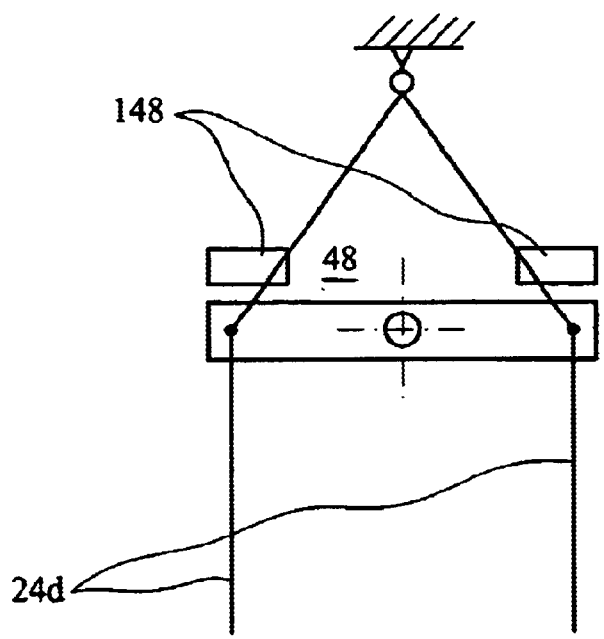
Figure 13:
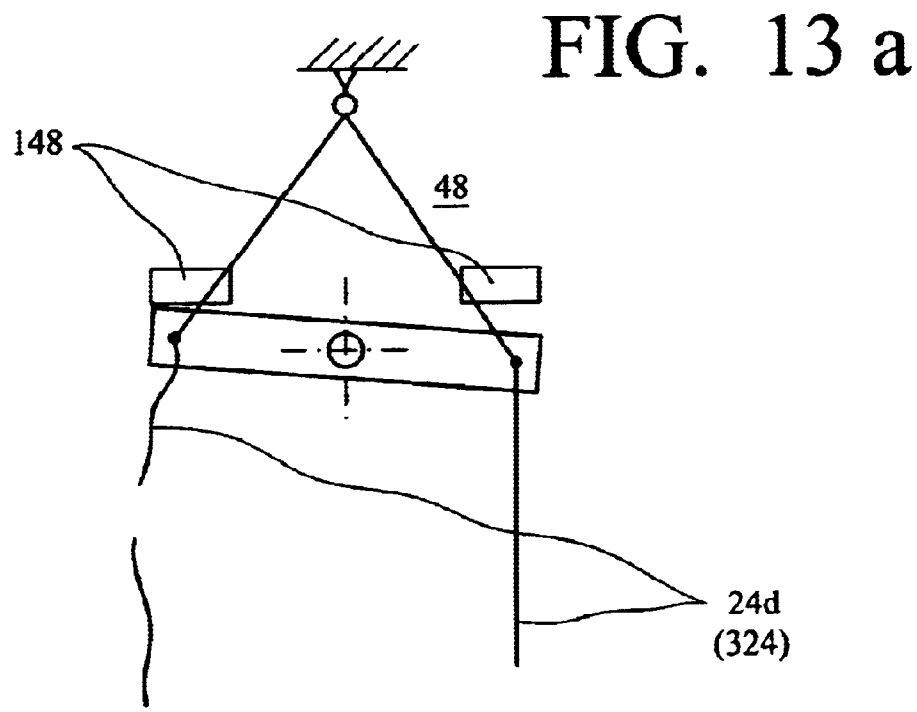

In the implementation which can be seen from FIGS. 13 and 13a, a rocker 48 which can be pivoted in the safety case (for example breakage of one of the two cables 24d) is provided. The pivoting movement of the rocker 48 is limited by a stop 148, so that the cable 24d which has then become the safety cable 324 cannot yield too far. On the other hand, the rocker 48 helps to compensate for any slight length differences, so that the two cables 24d carry the same load in the operating state.

In the sense of the invention, there are solutions in which a distinction cannot be drawn between working cables and safety cables, since in the normal operating state all the cables are in use and are under tension. In the safety case (that is to say when a cable breaks), the remaining cables each become a safety cable. In these designs, all the working cables are preferably monitored for breakage by means of sensors in order in the safety case to generate or to trigger appropriate information signals or braking signals.

In the case of such embodiments, the sensors operate in the opposite direction to that in the case of pure safety cables. In the case of the latter, they detect the build-up of a tension, in the case of the former they detect the drop in tension in the cable (breakage).

PARTS LIST

| | |
|---|---|
| 2 | Support arm and/or parallelogram carrier |
| 22 | Balance arm |
| 23 | Sliding pad |
| 24 | Cable pull |
| 24d | Working cable pull |
| 24f | Safety cable pull |
| 29a | Support arm |
| 35 | Bearing |
| 36, 36a | Roller |
| 37, 37a | Roller |
| 38 | Rotatable part of the deflecting roller 37a |
| 39 | Rigid or braked part of the deflecting roller 37a |
| 40 | Tension spring |
| 41 | Groove |
| 42 | Clamping and/or securing groove (wedge-shaped) |
| 43 | Safety jacket |
| 44 | Axis |
| 45 | Wedge brake |
| 46 | Wedge groove |
| 47 | Pressure and/or securing roller |
| 48 | Rocker |
| 49 | Roller body |
| 50 | Leaf spring |
| 51 | Cavity |
| 52 | Block and tackle |
| 55 | Block and tackle rollers |
| 56 | Block and tackle rollers |
| 57 | Brake; (comparable brakes can be provided on all axes of movement of the stand, preferably in the support arm 2 (parallelogram carrier) or in the pivoting carrier 79;) |
| 245 | Limit switch |
| 324 | Safety cable |
| 344 | Connecting cable |
| 345 | Limit switch |
| AGb | Balance weight |
| G | Load and/or weight of the microscope |
| F | Constant equilibrant |

What is claimed is:

1. In a stand having a pivotable support arm to accommodate a load and a working cable pull connected to said support arm for transmitting a balancing force to said support arm, the improvement comprising:
   a safety cable pull arranged to take over the function of said working cable pull in the event said working cable pull breaks; and
   a brake operatively arranged to engage said support arm.

2. In a stand having a pivotable support arm to accommodate a load and a working cable pull connected to said support arm for transmitting a balancing force to said support arm, the improvement comprising:
   a safety cable pull arranged to take over the function of said working cable pull in the event said working cable pull breaks, wherein said safety cable pull is normally untensioned but operates under tension in the event said working cable pull breaks.

3. In a stand having a pivotable support arm to accommodate a load and a working cable pull connected to said support arm for transmitting a balancing force to said support arm, the improvement comprising:
   a safety cable pull arranged to take over the function of said working cable pull in the event said working cable pull breaks, wherein said working cable pull and said safety cable pull run substantially parallel to one another.

4. The improvement recited in claim 2, further comprising a braking device for providing increased resistance to movement of said safety cable pull when said safety cable pull is under tension, whereby movement of said load is met with increased resistance.

5. The improvement recited in claim 2, further comprising at least one electronic switch that is actuated when said safety cable comes under tension.

6. The improvement recited in claim 5 wherein said switch is connected to at least one signal generator in order to activate said at least one signal generator when said safety cable comes under tension.

7. The improvement recited in claim 5 wherein said switch is connected to at least one controller in order to activate said at least one controller when said safety cable comes under tension.

8. The improvement recited in claim 5 wherein said switch is connected to at least one electromagnetic brake in order to activate said at least one electromagnetic brake when said safety cable comes under tension.

9. In a stand having a pivotable support arm to accommodate a load and a working cable pull connected to said support arm for transmitting a balancing force to said support arm, the improvement comprising:
   a safety cable pull arranged to take over the function of said working cable pull in the event said working cable pull breaks; and
   a deflecting roller having a first circumferential groove for receiving said working cable pull and a second circumferential groove parallel to said first circumferential groove for receiving said safety cable pull.

10. The improvement recited in claim 9, wherein said second circumferential groove is a clamping groove having opposing walls for contacting said safety cable pull and exerting increased friction thereon when said safety cable pull comes under tension.

11. The improvement recited in claim 9, wherein said roller includes a rotatable part having said first circumferential groove, and a poorly rotatable part adjacent said rotatable part, said rotatable part and said poorly rotatable part being configured to form said second circumferential groove therebetween, said second circumferential groove being in the form of a clamping groove for braking said safety cable pull when said safety cable pull comes under tension.

12. The improvement recited in claim 9, wherein said roller includes a rotatable part having said first circumferential groove, and a non-rotatable part adjacent said rotatable part, said rotatable part and said non-rotatable part being configured to form said second circumferential groove therebetween, said second circumferential groove being in the form of a clamping groove for braking said safety cable pull when said safety cable pull comes under tension.

13. The improvement recited in claim 11, further comprising a spring for biasing said poorly rotatable part axially towards said rotatable part and a brake device axially alongside said poorly rotatable part, whereby said safety cable pull displaces said poorly rotatable against the urging of said spring and into braked engagement with said brake device when said safety cable pull comes under tension.

14. The improvement recited in claim 11, wherein said second circumferential groove is covered by a safety jacket to prevent said untensioned safety cable pull from entering said groove, said safety jacket collapsing when safety cable pull comes under tension to permit said tensioned safety cable pull to enter and be grasped by said second circumferential groove.

15. The improvement recited in claim 2, further comprising a braking element having a clamping groove arranged proximate to said safety cable pull, wherein said safety cable pull does not contact said clamping groove when said safety cable pull is not tensioned and said safety cable pull comes into clamping contact with said clamping groove when said safety cable pull comes under tension.

16. The improvement recited in claim 15, further comprising a pressure roller arranged to bias said safety cable away from said clamping groove when said safety cable pull is not tensioned.

17. The improvement recited in claim 10, further comprising a brake operatively arranged to engage said deflecting roller.

18. The improvement recited in claim 2, further comprising a second working cable pull parallel to said working cable pull.

19. The improvement recited in claim 18, wherein each of said working cable pulls and said safety cable pull has a starting end and a finishing end, and said improvement further comprises a rocker accommodating said starting ends of said working cable pulls and said safety cable pulls.

20. The improvement recited in claim 2, further comprising a second working cable pull connected to said support arm, each of said working cable pulls being capable of transmitting said balancing force individually; and a plurality of sensors assigned at least one to each of said working cable pulls to monitor said working cable pulls for breakage.

21. The improvement recited in claim 20, wherein said plurality of sensors communicate a detected breakage of an associated working cable pull to a user.

22. The improvement recited in claim 20, wherein said plurality of sensors communicate a detected breakage of an associated working cable pull to brake control.

* * * * *